United States Patent [19]

Gorsuch et al.

[11] Patent Number: 5,224,926
[45] Date of Patent: Jul. 6, 1993

[54] TRANSVIVO PLASMA EXTRACTION CATHETER DEVICE

[75] Inventors: Reynolds G. F. Gorsuch, Yountville; John Atkin, Corona Del Mar, both of Calif.

[73] Assignee: Healthdyne, Inc., Marietta, Ga.

[21] Appl. No.: 745,912

[22] Filed: Aug. 16, 1991

Related U.S. Application Data

[63] Continuation-in-part of Ser. No. 570,002, Aug. 20, 1990, and a continuation-in-part of Ser. No. 570,009, Aug. 20, 1990, Pat. No. 5,151,082, and a continuation-in-part of Ser. No. 570,029, Aug. 20, 1990, Pat. No. 5,152,743, each is a continuation-in-part of Ser. No. 229,007, Aug. 5, 1988, Pat. No. 4,950,224.

[51] Int. Cl.⁵ .......................................... A61M 37/00
[52] U.S. Cl. .......................................... 604/4; 604/6; 604/53
[58] Field of Search ........................ 604/4-6, 604/7, 8, 52, 53, 403, 406, 27; 422/44, 48; 210/645, 646

[56] References Cited

U.S. PATENT DOCUMENTS 4,948,560 8/1990 Deguchi et al. ............... 422/48
4,950,224 8/1990 Gorsuch et al. ............... 604/4

FOREIGN PATENT DOCUMENTS 2606642 5/1988 France ........................ 604/4

Primary Examiner—Randall L. Green
Assistant Examiner—R. Clarke
Attorney, Agent, or Firm—Jerry R. Seiler

[57] ABSTRACT

A device for being implanted in a blood vessel for carrying out continuous in vivo plasma separation comprises an elongated, axial header and at least one elongated microporous fiber having a hollow interior, said fiber being dimensioned to be received within a blood vessel without significantly obstructing fluid flow through said blood vessel, the pore size of said fiber being sufficient to allow plasma to diffuse through said pores into said hollow interior of said fiber but not sufficient to allow cellular components larger than plasma to diffuse therethrough, said one or more fibers extending laterally relative to the axis of said header and in fluid communication with said header.

In another embodiment, the fibers comprise a drogue-shaped device comprising a plurality of said fibers aligned lengthwise, a first end of said fibers terminating substantially in first plane and generally forming an annulus having a first diameter, and a second end of said fibers terminating generally in a second plane and secured in an annular header having a second diameter smaller than said first diameter.

28 Claims, 3 Drawing Sheets

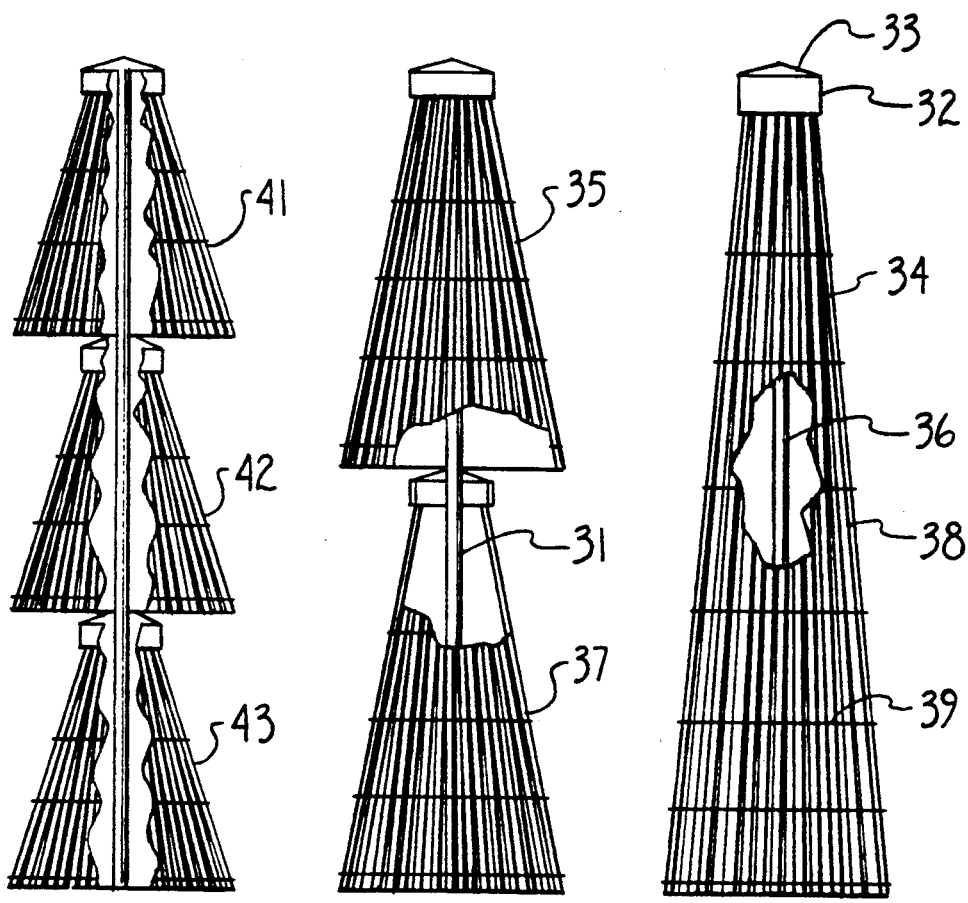

5,224,926

TRANSVIVO PLASMA EXTRACTION CATHETER DEVICE

This application is a continuation-in-part of Ser. Nos. 570,002, 570,009 now U.S. Pat. No. 5,151,082 and 570,029, now U.S. Pat. No. 5,152,243 filed Aug. 20, 1990, which applications are continuations-in-part of Ser. No. 229,007, filed Aug. 5, 1988, now U.S. Pat. No. 4,950,224.

BACKGROUND OF THE INVENTION

In the aforesaid applications and patent, there is disclosed an apparatus for in vivo separation of plasma from blood utilizing at least one elongated microporous fiber having a hollow interior for being received within a blood vessel without significantly obstructing fluid flow through the vessel. The fiber or fibers comprise a material having a porous size sufficient to allow plasma to diffuse through the pores into the hollow fiber interior but which pores prevent cellular components larger than plasma to diffuse or enter the fiber interior. The elongated fiber or fibers are in fluid communication with a catheter, preferably a dual lumen catheter having a first tube which permits passage of the plasma from the fiber, and a second hollow tube which returns plasma to the blood vessel. Various systems, apparatus and methods for use of the aforesaid fiber technology including measurement of blood parameters, kidney dialysis, and separation and removal of a substantial number of materials are disclosed. The disclosure of the aforesaid fibers, the systems and methods of use in the aforesaid applications and patent are incorporated herein by reference.

In the aforesaid patent and applications, the portion of the apparatus and systems comprising the fiber or fibers implanted in a blood vessel are illustrated as extending somewhat loosely and non-uniformly or randomly lengthwise, generally parallel with the direction of blood flow in the vessel or vein. According to the present invention, it has been found that such a fiber disposition is not the most efficient for achieving relatively high or preferred plasma diffusion rates. It is to the improvement of such fiber elements or devices and apparatus design that the present invention is directed.

SUMMARY OF THE INVENTION

The present invention provides an improved plasma extraction fiber arrangement, the design and/or configuration to provide fiber-catheter devices for achieving improved efficiency in vivo plasma separation. The improved designs include drogue and bottlebrush-type design configurations.

BRIEF DESCRIPTION OF THE DRAWINGS

FIGS. 7, 8 and 9 illustrate different drogue design embodiments.

DETAILED DESCRIPTION OF THE INVENTION

In the aforesaid incorporated applications and patent disclosures, the fibers used for in vivo diffusion of plasma from blood are disclosed as comprising a polymeric plastic, preferably polypropylene. Optimum characteristics of a suitable material require biocompatibility and flexibility, together with non-thrombogenic, non-clotting qualities and with a fiber-pore size between about 0.1 and about 1.0 $\mu$m. Additionally, the material must be either hydrophilic or capable of being converted to a hydrophilic material. According to the invention, it has now been found that a high flux coefficient of greater than about 1.8 ml/min/sq cm/0.1 bar is desired for most applications. However, flux coefficients between about 0.8 and about 2.5 are useful in a number of applications. The flux coefficient is the rate of plasma diffusion, and is substantially dependent on the number of holes or pores per unit fiber length per mm Hg of the trans membrane pressure, with the higher the number, the more preferred the material and the more efficient the process of plasma separation using the fibers pursuant to the invention.

In addition to the aforesaid flux coefficient, other factors and parameters of the design characteristics, fiber arrangement and configuration are also to be considered and optimized. The designs, arrangements or configuration of the fiber or fibers in the elements or devices of the present invention are intended to optimize at least a portion of these important factors. More specifically, it has been found that shear rate, which is characterized by the local blood velocity per unit length at the fiber interface, is dependent on the angle that the fiber intersects the direction or axis of blood flow, and the position of the individual fiber segment in the vessel blood velocity profile. The preferred fiber disposition angle relative to the direction of blood flow at the point of contact of 90° is optimal. Thus, apparatus or fiber element configurations where the angle of intersect of the fiber axis to blood flow direction approaches 90°, are preferred. The configuration, and design characteristics of the fiber element construction which minimizes the distortion of the blood velocity profile, must also be considered. Designs incorporating fibers that are too close together or which are shaded from blood flow by other fibers will reduce shear rate and reduce blood velocity, the combination of which may result in less efficient plasma extraction. The fiber length is also a factor to be considered, with relatively long fibers or bundles of long fibers resulting in an unacceptable pressure gradient for extracting plasma because of reduced blood flow and concomitant areas of local stagnation.

Figure 1:
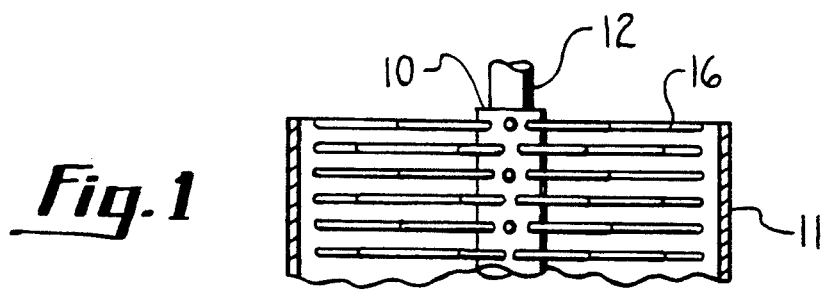
FIG. 1 illustrates a side view of a first bottlebrush-type embodiment of the present invention.

In FIG. 1 there is illustrated a bottlebrush-type fiber/catheter design incorporating a plurality of single hollow fibers 16 extending laterally, preferably substantially normal, to the axis of elongated header 10. The individual fibers 16 extend radially and laterally, preferably substantially normal, relative to the axis of elongated header 10, which is secured to dual lumen catheter 12. The hollow fibers are in fluid communication with the header and the catheter. The vessel or vein wall 11 is illustrated schematically, it being appreciated that the ends of the fibers are preferably separated from the vessel wall to reduce interference with blood flow and minimize distortion of the local blood velocity profile at the fiber device. The fibers are preferably of equal length, as shown, or then may be of different lengths. However, an important feature of the bottlebrush design shown minimizes shading of downstream adjacent fibers by avoiding overlapping by adjacent upstream fibers along the direction of blood flow. As will be evident from the drawings, where the fibers extend substantially or generally normal to the axis of elongated header 10, a 90° optimum fiber angle, or nearly 90° fiber angle, relative to the axis or direction of blood flow is achieved. However, other angles between about 45° and about 135° may also be acceptable. The fibers may extend radially in a pattern spaced radially and axially along the header length or the fibers may be randomly spaced, radially and/or axially.

Figure 2:
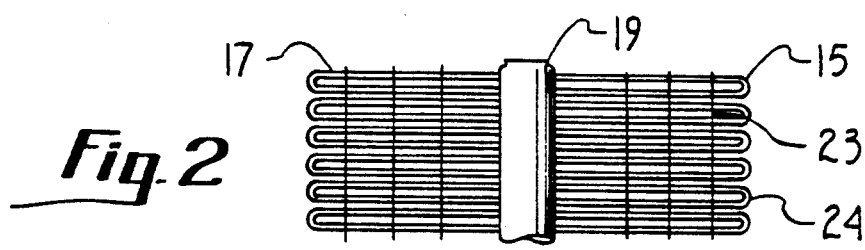
FIG. 2 is a side view illustrating a second bottlebrush-type embodiment fiber configuration.
Figure 3:
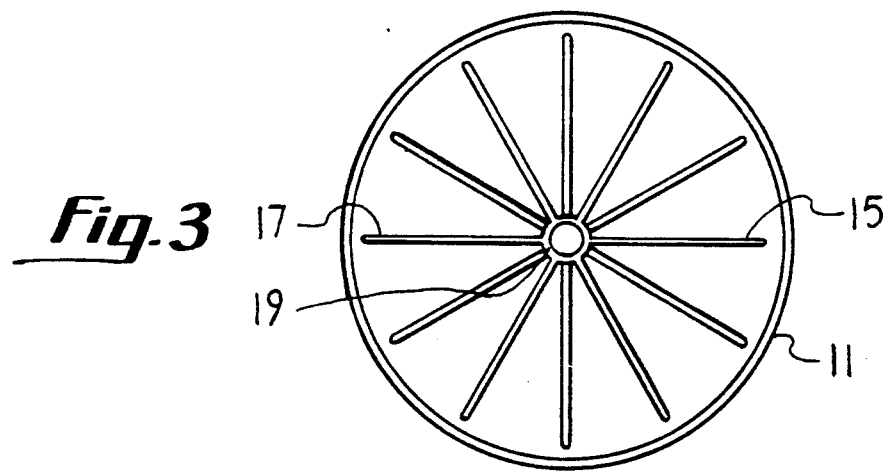
FIG. 3 is a top view of a device of the invention incorporating a plurality of fiber embodiments of FIG. 2.

In FIG. 2, there is illustrated another bottlebrush-type configuration using a fiber ribbon 24, comprising a plurality of fibers 17 extending radially and axially along elongated header 19. A plurality of fibers 15 and 17 of ribbon 24 are shown extending from opposite sides of the header. The ends of the fibers are secured in the header and are in fluid communication with its hollow interior. Threads 23 assist in preventing distortion of the fiber ribbon. In a device incorporating this ribbon bottlebrush embodiment, a plurality of ribbons are used, with the ribbon walls or ribs extending radially from an elongated header 19 as illustrated in FIG. 3. The ribbons are preferably evenly spaced around the header, with any suitable number of ribbons used. It has been found, according to the invention, that between about 10 and about 20 ribbons are especially preferred, and 16 most preferred. It has also been found, that in using such a design, although the fibers in each ribbon are aligned substantially in a single plane parallel along the header axis and direction of blood flow, the design results in quite effective plasma diffusion due to currents and eddies formed between the ribbons.

In forming devices shown in FIGS. 1-4, the open fiber ends are secured in an elongated header using potting and layup techniques known to those skilled in the art. For example, the fibers or ribbons may be arranged in a tool around a center core device, with the header formed around the core. The header is then secured to a dual lumen catheter.

Figure 4:
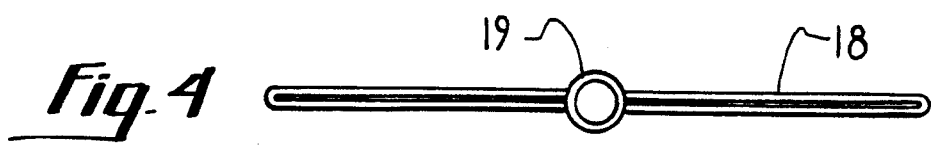
FIG. 4 illustrates an alternative useful fiber configuration.

FIG. 4 shows an alternative configuration in which a fiber 18 is formed with a side-by-side fiber fold, both segments of the fiber length being substantially parallel in a plane generally perpendicular to the header 19 axis. A design of FIG. 4, may be used in the configurations illustrated in FIGS. 1 and 3. In addition, multiple fiber lengths and/or folds may be used, and the double length configuration of FIG. 4 is but one example of such an embodiment.

Figure 5:
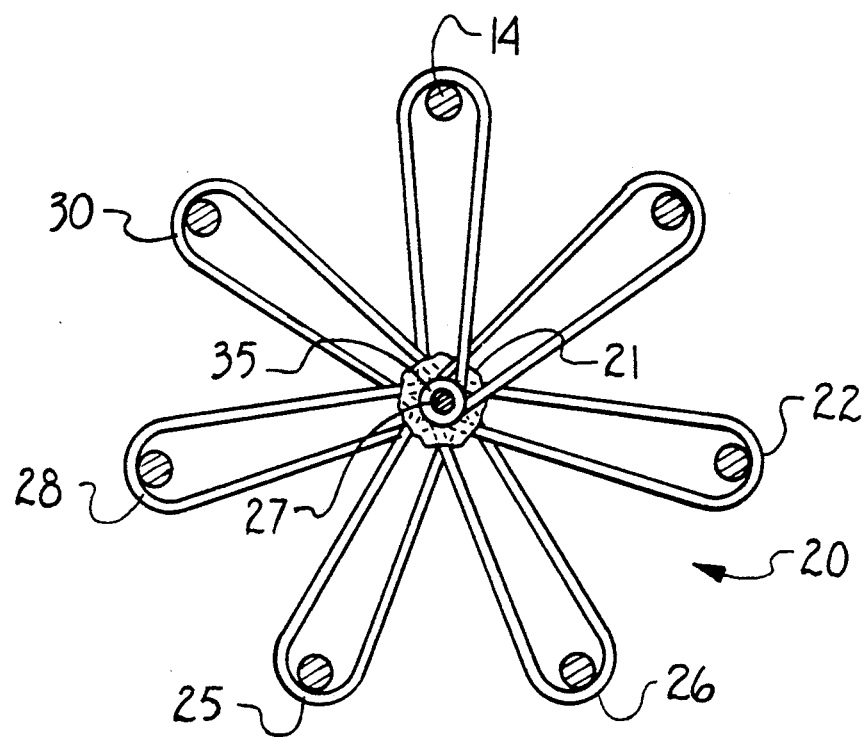
FIGS. 5 and 6 illustrate top and side views of another bottlebrush-type embodiment.
Figure 6:
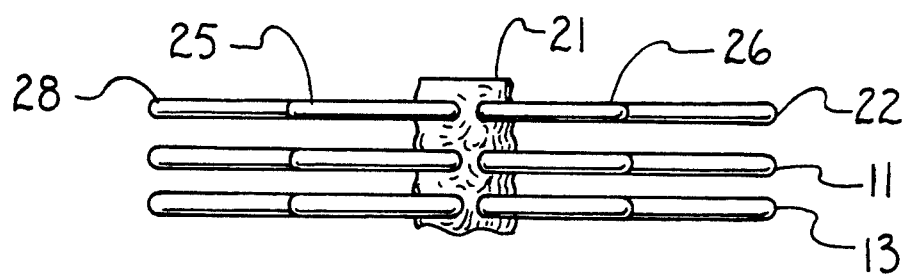

In FIGS. 5 and 6, there is illustrated an alternative bottlebrush-type design in which a fiber 20 is configured in a plurality of lobes, each fiber lobe being secured along and in fluid communication with header 21. This star-like configuration may be achieved by wrapping a fiber length on pins or pegs 14, preferably evenly spaced from a central pin 27, around which the fiber is wound to achieve the structure illustrated in FIG. 5. Winding is continued until the desired layers of lobed fibers are achieved. With the pins 14 around which the fiber lobes are formed still in place, a header 21 is formed by directing a suitable material, preferably a polyurethane composition, toward the center pin between each pair of adjacent lobes. The header forming material may also be deposited at the center core as each loop or loop assembly of fiber is wound around the center pin. The header plastic build-up along the length of the center pin is continued until the elongated polyurethane header is produced. An annular cutting tool, such as a commercial paper punch or drill is then urged along the center pin forming a central lumen 35 and cutting the ends of the fiber lobes in open, fluid communication with the hollow interior lumen 35 of header 21. The header then is secured appropriately to a catheter previously described. In the preferred construction, the fiber lobes extend outwardly radially substantially normal to the catheter axis. In FIG. 6 there are illustrated four layers or lobes. The lobes may be axially oriented to avoid overlapping or shading of downstream adjacent fiber lobes or they may be in layers of superimposed, substantially identical lobe patterns.

FIGS. 7, 8 and 9 illustrate different embodiments of a drogue design. In this design, the hollow fibers are woven into a belt held together by cross weave threads. The belt is formed into a tube shape and the ends joined by a cured adhesive. The end of the tube is folded into a funnel shape and potted into a header with a casting material, preferably polyurethane, along with the end of the central core catheter. The end of the assembly is cut off, exposing the central lumens of the fibers and catheter, and the end is terminated with a molded end cap which provides the access from fiber lumen to catheter lumen.

In FIG. 7, a single element is illustrated with a plurality of fibers 38 woven together using cross weave threads 39 with the fiber ends at one end of the belt folded along folds 34 and potted into header 32 provided with a molded end cap 33. Catheter 36 is shown extending inside of the element with a portion of the fabric cut away for illustration. In FIG. 8, pair of elements 35 and 37, constructed substantially like that of FIG. 5, are connected in series along catheter 31. In FIG. 9, three elements 41, 42 and 43 connected in series along a common catheter are illustrated. Any number of such elements may be combined. The apparatus of this design may be used with the open ends of the drogue upstream or downstream relative to the blood stream flow in a vein. The advantage of the larger diameter opening being upstream is that the pressure of blood flow will open the element in an "umbrella"-type effect. The disadvantage is that it may require retrograde removal surgically via the inferior vena cava. Where the drogue design is used in the opposite orientation relative to blood flow, the advantage is simple upstream removal from the patient but the device requires stiffeners to hold the fiber element open against hydraulic blood flow pressure. It will also be understood that interference with the blood flow will depend somewhat on the number of fibers used in each of the elements. Although more fibers will result in a greater potential plasma diffusion, the rates may also be adversely affected by reduced blood flow around the greater number of fibers. Moreover, shading, as well as the relatively disadvantageous angle of the fibers relative to the direction of blood flow, further reduces efficiency of this configuration.

In an apparatus or system using the fiber element devices of the invention, plasma is extracted from the blood along the length of each fiber and is transmitted to the header down the open center core of the fiber. The header then accumulates the plasma and provides a conduit for the extracted plasma to one of the lumens in the attached catheter for conduction to the ex-vivo treatment system, of the type disclosed in the aforesaid patent and applications, incorporated herein by reference. The header forms the second function of encapsulating the fiber and holding it attached to the extraction element. The header material must be biocompatible, non-thrombogenic, and compatible with the fiber and catheter material. The header material must also be moldable or castable so that the assembly can be fabricated in a desirable or appropriate shape. A preferred header material comprises a pre-mixed polyurethane which can be applied and built up around a mandril, or molded according to techniques known in the art.

The devices disclosed herein must be collapsible to a minimal diameter before being implanted or installed via the subclavian or jugular veins. The use of a sleeve as previously disclosed in the aforesaid applications, which can be withdrawn after installation, is preferred. A preferred site for locating and placing the devices is in the superior vena cava. Such a location is convenient for being connected to treatment apparatus. Because the vena cava site is only about 3.5 inches long between the subclavian junction and right atrium, and 4 inches long if the jugular vein is used, the devices including the header, fiber and catheter, are restricted to such a maximum length. While it is apparent that the device could be longer than 4 inches, if permitted to enter the left atrium of the heart, it may not be considered to be good medical practice due to potential stimulation of the sinoatrial node.

We claim:

1. A device for being implanted in a blood vessel for carrying out continuous in vivo plasma separation comprising an elongated, axial header having an elongated exterior surface, and at least one elongated microporous fiber having a hollow interior, said fiber being dimensioned to be received within a blood vessel without significantly obstructing fluid flow through said blood vessel, the pore size of said fiber being sufficient to allow plasma to diffuse through said pores into said hollow interior of said fiber but not sufficient to allow cellular components larger than plasma to diffuse therethrough, said one or more fibers secured along and extending from said elongated exterior surface of said header and extending laterally relative to the axis thereof, and in fluid communication with said header.

2. A device of claim 1 wherein said fiber comprises a plurality of looped branches.

3. A device of claim 2 wherein said branches extend substantially normal and radially from said header.

4. A device of claim 1 wherein said fiber comprises a plurality of fibers extending substantially normal and radially from said header.

5. A device of claim 4 wherein said fibers comprise a plurality of substantially planar ribs extending radially from said header.

6. A device of claim 5 wherein the plane of each of said planar ribs lies substantially parallel with the axis of said header.

7. A device of claim 1 wherein said one or more of said fibers extend substantially radially from said header in the form of a pattern and wherein said pattern for each of said devices is substantially identical.

8. A device of claim 1 comprising a plurality of said fibers each having a first end secured in said header.

9. A device of claim 1 wherein said fibers have a flux coefficient of between about 0.8 and about 2.5 ml/min/sqcm/0.1 bar.

10. A device of claim 1 wherein said fibers have a flux coefficient of at least 1.8 ml/min/sq cm/0.1 bar.

11. A device of claim 1 wherein said fiber is composed of a polymeric material.

12. A device of claim 11 wherein said polymeric material is polypropylene.

13. A device of claim 11 wherein said fiber has a pore size of from about 0.1 to 1.0 $\mu$m.

14. An apparatus comprising the device of claim 1 wherein said hollow interior of said elongated fibers is in fluid communication with a means for conducting plasma comprising a first discrete hollow tube which connects to one end of the fibers and permits passage of plasma from said hollow interior of said fibers and a second discrete hollow tube which returns plasma to said blood vessel such that plasma being removed from said fibers is kept separated from plasma being returned to the blood vessel.

15. An apparatus of claim 14, further comprising a treatment system in fluid communication with said fibers, whereby selected subcomponents of said plasma removed from said blood vessel are treated and the treated plasma returned to said blood vessel.

16. In an apparatus for continuous in vivo plasma separation, comprising:
at least one elongated microporous fiber having a hollow interior, said fiber being dimensioned to be received within a blood vessel without significantly obstructing fluid flow through said blood vessel, the pore size of said fiber being sufficient to allow plasma to diffuse through said pores into said hollow interior of said fiber but not sufficient to allow cellular components larger than plasma to diffuse therethrough, the improvement comprising a drogue-shaped device comprising a plurality of said fibers aligned lengthwise, a first end of said fibers terminating substantially in first plane and generally forming an annulus having a first diameter, and a second end of said fibers terminating generally in a second plane and secured in an annular header having a second diameter smaller than said first diameter.

17. An apparatus of claim 16 wherein said header is in fluid communication with the interior of said fibers.

18. An apparatus of claim 17 including a catheter secured in said header and in fluid communication therewith.

19. An apparatus of claim 16 wherein said device comprises a single layer of adjacent fibers along said annulus.

20. An apparatus of claim 19 wherein said fibers are overlapped adjacent said annular header.

21. An apparatus of claim 18 comprising a plurality of said devices secured axially in series along said catheter.

22. Apparatus of claim 16 wherein said fibers have a flux coefficient of between about 0.8 and about 2.5 ml/min/sq cm/0.1 bar.

23. An apparatus of claim 16 wherein said fibers have a flux coefficient of at least 1.8 ml/min/sq cm/0.1 bar.

24. The apparatus of claim 16 wherein said fiber is composed of a polymeric material.

25. The apparatus of claim 24 wherein said polymeric material is polypropylene.

26. The apparatus of claim 25 wherein said fiber has a pore size of from about 0.1 to 1.0 $\mu$m.

27. The apparatus of claim 16 wherein said hollow interior of said elongated fibers is in fluid communication with a means for conducting plasma comprising a first discrete hollow tube which connects to one end of the fibers and permits passage of plasma from said hollow interior of said fibers and a second discrete hollow tube which returns plasma to said blood vessel such that plasma being removed from said fibers is kept separated from plasma being returned to the blood vessel.

28. The apparatus of claim 27, further comprising a treatment system in fluid communication with said fibers, whereby selected subcomponents of said plasma removed from said blood vessel are treated and the treated plasma returned to said blood vessel.

* * * * *